(12) United States Patent
Bogdan et al.

(10) Patent No.: US 7,301,064 B1
(45) Date of Patent: Nov. 27, 2007

(54) ETHYLBENZENE CONVERSION AND XYLENE ISOMERIZATION PROCESSES AND CATALYSTS THEREFOR

(75) Inventors: Paula L. Bogdan, Mount Prospect, IL (US); Patrick C. Whitchurch, Villa Park, IL (US); Robert B. Larson, Chicago, IL (US); James E. Rekoske, Glenview, IL (US); Dimitri A. Trufanov, Arlington Heights, IL (US); Victor C. Patton, Darien, IL (US); Suheil F. Abdo, Lincolnshire, IL (US)

(73) Assignee: UOP LLC, Des Plaines, IL (US)

( * ) Notice: Subject to any disclaimer, the term of this patent is extended or adjusted under 35 U.S.C. 154(b) by 210 days.

(21) Appl. No.: 11/225,976

(22) Filed: Sep. 14, 2005

(51) Int. Cl.
 C07C 5/29 (2006.01)
 C07C 4/12 (2006.01)
(52) U.S. Cl. ............... 585/480; 585/481; 585/489
(58) Field of Classification Search ............ 585/480, 585/481, 489
 See application file for complete search history.

(56) References Cited

U.S. PATENT DOCUMENTS

| 3,201,491 | A | 8/1965 | Stine et al. .................. 260/676 |
|---|---|---|---|
| 3,626,020 | A | 12/1971 | Neuzil .................. 260/674 SA |
| 3,696,107 | A | 10/1972 | Neuzil .................. 260/674 SA |
| 4,039,599 | A | 8/1977 | Gewartowski .......... 260/668 A |
| 4,184,943 | A | 1/1980 | Anderson ............... 208/310 R |
| 4,310,440 | A | 1/1982 | Wilson et al. ............. 252/435 |
| 4,362,653 | A | 12/1982 | Robinson ................ 252/455 R |
| 4,381,419 | A | 4/1983 | Wylie ......................... 585/828 |
| 4,402,832 | A | 9/1983 | Gerhold ..................... 210/659 |
| 4,440,871 | A | 4/1984 | Lok et al. ................... 502/214 |
| 4,629,717 | A | 12/1986 | Chao .......................... 502/208 |
| 4,793,984 | A | 12/1988 | Lok et al. ................... 423/306 |
| 4,899,012 | A | 2/1990 | Sachtler et al. ............. 585/482 |
| 6,143,941 | A | 11/2000 | Sharma et al. ............. 585/481 |
| 6,573,418 | B2 | 6/2003 | Miller et al. ................ 585/826 |

Primary Examiner—Thuan D Dang
(74) Attorney, Agent, or Firm—Maryann Maas

(57) ABSTRACT

Catalysts comprising a combination of molecular sieve having a pore diameter of from about 4 to 8 angstroms and a catalytically-effective amount of molybdenum hydrogenation component in an amorphous aluminum phosphate binder provide processes for isomerizing xylene and dealkylating ethylbenzene in feed streams that exhibit stability, selectivity and low ring loss.

10 Claims, No Drawings

ETHYLBENZENE CONVERSION AND XYLENE ISOMERIZATION PROCESSES AND CATALYSTS THEREFOR

FIELD OF THE INVENTION

This invention relates to catalysts and catalytic processes for the isomerization of xylenes and for the conversion of ethylbenzene by dealkylation in the presence of hydrogen, particularly such catalysts using a combination of molecular sieve and molybdenum and their use to enhance isomerization activity while retaining ethylbenzene dealkylation activity, low transalkylation activity and low aromatic ring loss to naphthenes.

BACKGROUND OF THE INVENTION

Numerous processes have been proposed for the isomerization of one or more of xylenes (meta-xylene, ortho-xylene and para-xylene) to form other isomers of xylene. In many instances, the sought xylene isomer is para-xylene due to the demand for terephthalic acid for the manufacture of polyester.

In general, these xylene isomerization processes comprise contacting the xylene isomer sought to be isomerized with an isomerization catalyst under isomerization conditions. Various catalysts have been proposed for xylene isomerization. These catalysts include molecular sieves, especially molecular sieves contained in a refractory, inorganic oxide matrix. The catalysts also contain a hydrogenation metal component.

Due to the large scale of commercial facilities to produce para-xylene on an economically competitive basis, not only must a xylene isomerization process be active and stable, but it also must not unduly crack the aromatic feed so as to result in ring loss. Moreover, the isomerization processes produce by-products such as benzene, toluene, and aromatics having 9 or more carbon atoms. Often the xylene-containing feed to be isomerized also contains ethylbenzene. Ethylbenzene may be dealkylated, or the ethylbenzene can be converted by isomerization or transalkylation. Whether the isomerization process will dealkylate or will convert ethylbenzene depends upon the isomerization conditions including catalyst.

Where the ethylbenzene is sought to be dealkylated, several concerns exist. First, the dealkylation should be selective to the ethylbenzene and not cause undue loss of xylene. Second, the isomerization and ethylbenzene conversion should not result in undue production of transalkylated products such as toluene and trimethylbenzene. Third, the dealkylation should not cause the production of naphthenes that would contaminate any benzene stream separated from the product of the isomerization and ethylbenzene conversion, and thus reduce the value of the benzene.

Catalysts containing molybdenum provide advantageously low production of naphthenes. However, they do not exhibit a good balance between xylene isomerization and ethylbenzene dealkylation. A catalyst exhibiting good ethylbenzene conversion provides a low ratio of para-xylene to total xylenes. If the concentration of molybdenum is increased, some improvement can be obtained in xylene isomerization, but at a cost in ethylbenzene conversion activity.

Another difficulty with molybdenum-containing catalysts is that the xylene isomerization activity deteriorates with decreasing hydrogen partial pressure to an undesirable extent. Consequently, such a catalyst would not be useful in xylene isomerization facilities that use lower pressures.

U.S. Pat. No. 4,362,653, for instance, discloses a hydrocarbon conversion catalyst which could be used in the isomerization of isomerizable alkylaromatics that comprises silicalite (having an MFI-type structure) and a silica polymorph. The catalyst may contain optional ingredients. Molybdenum is listed as one of the many optional ingredients. U.S. Pat. No. 4,899,012 discloses catalyst for isomerization and conversion of ethylbenzene containing a Group VIII metal, lead, a pentasil zeolite and an inorganic oxide binder. U.S. Pat. No. 6,573,418 discloses a pressure swing adsorption process to separate para-xylene and ethylbenzene from $C_8$ aromatics. Included among the catalysts disclosed for ethylbenzene isomerization are those containing ZSM-5 type of molecular sieve (AI-MFI) dispersed on silica. The catalysts contain a hydrogenation metal and listed among the hydrogenation metals are molybdenum. Suitable matrix materials are said to be alumina and silica. See example 12 which uses a molybdenum-containing catalyst for xylene isomerization.

A catalyst using molybdenum tends to generate less naphthenes than a platinum-containing catalyst. However, at comparable ethylbenzene conversions, the molybdenum-containing catalysts have been inferior to platinum-containing catalysts in isomerization activity, i.e., yields a xylene product distribution not as close to equilibrium as are the products using a platinum-containing catalyst. Hence, platinum-containing catalysts have been preferred for commercial use. Catalysts are sought that provide the combination of the low naphthene generation achievable with molybdenum catalysts with good ethylbenzene conversion and isomerization activity. Moreover, catalysts are sought that can be used in a xylene isomerization facility regardless of whether it operates at lower pressures, e.g., about 700 pKa, or higher pressures, e.g., 1500 kPa.

SUMMARY OF THE INVENTION

In accordance with this invention, molybdenum-containing catalysts and processes for using the catalysts are provided for the isomerization of xylene and the dealkylation of ethylbenzene that exhibit not only desirable ethylbenzene conversion activity but also desirable isomerization activity, i.e., approach to xylene equilibrium distribution, while retaining low naphthene generation activity. Hence, the advantages provided by the catalysts of the invention can render them viable alternatives to platinum-containing catalysts. The improvement in molybdenum-containing catalysts provided by this invention resides in subjecting the catalyst to sufficient sulfiding to enhance the xylene isomerization activity of the catalyst.

The catalysts in accordance with this invention have a combination of a catalytically-effective amount of molecular sieve having a pore diameter of from about 4 to 8 angstroms, preferably a pentasil structure zeolite, e.g., MFI-type zeolite, and a catalytically-effective amount of molybdenum hydrogenation component which has been subjected to sufficient sulfiding to enhance the xylene isomerization activity of the catalyst. The sulfiding of the catalyst may be effected during at least one of (i) the preparation of the catalyst, (ii) regeneration of the catalyst or (iii) use of the catalyst in an isomerization process. Often the catalyst comprises sulfur in a S:Mo atomic ratio of up to about 3:1, preferably about 0.01:1 to 3:1, and most preferably about 0.1:1 to 2:1.

The broad aspects of the processes of this invention comprise contacting a feed stream containing a non-equilibrium admixture of at least one xylene isomer and ethylbenzene, wherein preferably between about 1 and 60, and more frequently between about 5 and 35, mass-% of the feed stream is ethylbenzene, with a catalyst comprising a catalytically-effective amount of the catalysts of this invention to provide an isomerization product having a reduced ethylbenzene concentration and an isomerized xylene distribution. The isomerization conditions include the presence of hydrogen in a mole ratio to hydrocarbon of between about 0.5:1 to 6:1, preferably 2:1 to 5:1. Preferably, the isomerization is conducted under at least partially vapor phase conditions. In the preferred aspects of the processes of this invention, the ethylbenzene conversion is at least about 60 mass-% and the xylene distribution is at least 90, preferably at least about 95, percent of equilibrium. Often, the naphthene net make is less than 0.02 mass-% based on the xylenes and ethylbenzene in the feed.

DETAILED DESCRIPTION OF THE INVENTION

The Catalyst

The catalysts used in the processes of this invention comprise a molecular sieve having a pore diameter of from about 4 to 8 angstroms, and a molybdenum hydrogenation component in an amorphous aluminum phosphate binder. Examples of molecular sieves include those having $Si:Al_2$ ratios greater than about 10, and often greater than about 20, such as the MFI, MEL, EUO, FER, MFS, MTT, MTW, TON, MOR, UZM-8 and FAU types of zeolites. Pentasil zeolites such as MFI, MEL, MTW and TON are preferred, and MFI-type zeolites, such as ZSM-5, silicalite, Borolite C, TS-1, TSZ, ZSM-12, SSZ-25, PSH-3, and ITQ-1 are especially preferred.

The zeolite is combined with binder for convenient formation of catalyst particles. The relative proportion of zeolite in the catalyst may range from about 1 to about 99 mass-%, with about 2 to about 90 mass-% being preferred.

The binder should be uniform in composition and relatively refractory to the conditions used in the process. Suitable binders include inorganic oxides such as one or more of alumina, aluminum phosphate, magnesia, zirconia, chromia, titania, boria and silica. The catalyst also may contain, without so limiting the composite, one or more of (1) other inorganic oxides including, but not limited to, beryllia, germania, vanadia, tin oxide, zinc oxide, iron oxide and cobalt oxide; (2) non-zeolitic molecular sieves, such as the aluminophosphates of U.S. Pat. No. 4,310,440, the silicoaluminophosphates of U.S. Pat. No. 4,440,871 and ELAPSOs of U.S. Pat. No. 4,793,984; and (3) spinels such as $MgAl_2O_4$, $FeAl_2O_4$, $ZnAl_2O_4$, $CaAl_2O_4$, and other like compounds having the formula $MO-Al_2O_3$ where M is a metal having a valence of 2; which components can be added to the composite at any suitable point.

A preferred binder or matrix component comprises an amorphous phosphorous-containing alumina (hereinafter referred to as aluminum phosphate) component. The atomic ratios of aluminum to phosphorus in the aluminum phosphate binder/matrix generally range from about 1:10 to 100:1, and more typically from about 1:5 to 20:1. Preferably the aluminum phosphate has a surface area of up to about 450 $m^2/g$, and preferably the surface area is up to about 250 $m^2/g$. See, for instance, U.S. Pat. No. 6,143,941.

When used, the amount of the aluminum phosphate binder is preferably sufficient to reduce the transalkylation activity of the catalyst, e.g., co production of toluene and trimethylbenzene. The preferred catalysts of this invention can be characterized as having under specified conditions, a net make of toluene and trimethylbenzene of less than about 3, preferably less than about 2, mass-% based on the mass of $C_8$ aromatics (xylenes and ethylbenzene) in the feed. The Evaluation Conditions for this characterization comprise using feed stream containing 15 mass-% ethylbenzene, 25 mass-% ortho-xylene and 60 mass-% meta-xylene; a hydrogen to hydrocarbon ratio of 4:1; a pressure of 700 kPa gauge; a weight hourly space velocity of 10 $hr^{-1}$, and a temperature sufficient to convert 75 mass-% of the ethylbenzene with the data taken at 50 hours of operation. These specified conditions are for the purpose of providing common conditions for catalyst evaluation and are not limiting as to the xylene isomerization conditions that may be used in the processes of this invention.

The aluminum phosphate may be prepared in any suitable manner. One suitable technique for preparing aluminum phosphate is the oil-drop method of preparing the aluminum phosphate which is described in U.S. Pat. No. 4,629,717. This technique involves the gellation of a hydrosol of alumina which contains a phosphorus compound using the well-known oil-drop method. Generally this technique involves preparing a hydrosol by digesting aluminum in aqueous hydrochloric acid at reflux temperatures of about 80° to 105° C. The mass ratio of aluminum to chloride in the sol often ranges from about 0.7:1 to 1.5:1. A phosphorus compound is added to the sol. Preferred phosphorus compounds are phosphoric acid, phosphorous acid and ammonium phosphate. The relative amount of phosphorus and aluminum expressed in atomic ratios ranges from about 10:1 to 1:100, and often 10:1 to 1:10.

If desired, the molecular sieve can be added to the hydrosol prior to gelling the mixture. One method of gelling involves combining a gelling agent with the mixture and then dispersing the resultant combined mixture into an oil bath or tower which has been heated to elevated temperatures such that gellation occurs with the formation of spheroidal particles. The gelling agents which may be used in this process are hexamethylene tetraamine, urea or mixtures thereof. The gelling agents release ammonia at the elevated temperatures which sets or converts the hydrosol spheres into hydrogel spheres. The spheres are then continuously withdrawn from the oil bath and typically subjected to specific aging and drying treatments in oil and in ammoniacal solution to further improve their physical characteristics. The resulting aged and gelled particles are then washed and dried at a relatively low temperature of about 100° to 150° C. and subjected to a calcination procedure at a temperature of about 450° to 700° C. for a period of about 1 to 20 hours.

The combined mixture preferably is dispersed into the oil bath in the form of droplets from a nozzle, orifice or rotating disk. Alternatively, the particles may be formed by spray-drying of the mixture at a temperature of from about 425° to 760° C. In any event, conditions and equipment should be selected to obtain small spherical particles; the particles preferably should have an average diameter of less than about 5.0 mm, more preferably from about 0.2 to 3 mm, and optimally from about 0.3 to 2 mm.

Alternatively, the catalyst may be an extrudate. The well-known extrusion method initially involves mixing of the molecular sieve with optionally the binder and a suitable peptizing agent to form a homogeneous dough or thick paste having the correct moisture content to allow for the formation of extrudates with acceptable integrity to withstand direct calcination. Extrudability is determined from an analysis of the moisture content of the dough, with moisture content in the range of from about 30 to about 50 mass-% being preferred. The dough is then extruded through a die pierced with multiple holes and the spaghetti-shaped extrudate is cut to form particles in accordance with techniques well known in the art. A multitude of different extrudate shapes is possible, including, but not limited to, cylinders, cloverleaf, dumbbell and symmetrical and asymmetrical polylobates. It is also within the scope of this invention that the extrudates may be further shaped to any desired form, such as spheres, by marumerization or any other means known in the art.

Another alternative is to use a composite structure having a core and an outer layer containing molecular sieve and aluminum phosphate. Often, the thickness of the molecular sieve layer is less than about 250 microns, e.g., 20 to 200, microns. The core may be composed of any suitable support material such as alumina or silica, and is preferably relatively inert towards dealkylation. Advantageously, at least about 75, and preferably at least about 90, mass-% of the molybdenum in the catalyst is contained in the outer layer. The catalyst may be in any suitable configuration including spheres and monolithic structures.

The catalyst may contain other components provided that they do not unduly adversely affect the performance of the finished catalyst. These components are preferably in a minor amount, e.g., less than about 40, and most preferably less than about 15, mass-% based upon the mass of the catalyst. These components include those that have found application in hydrocarbon conversion catalysts such as: (1) refractory inorganic oxides such as alumina, titania, zirconia, chromia, zinc oxide, magnesia, thoria, boria, silica-alumina, silica-magnesia, chromia-alumina, alumina-boria, silica-zirconia, phosphorus-alumina, etc.; (2) ceramics, porcelain, bauxite; (3) silica or silica gel, silicon carbide, clays and silicates including those synthetically prepared and naturally occurring, which may or may not be acid treated, for example, aftapulgite clay, diatomaceous earth, fuller's earth, kaolin, kieselguhr, etc.; and (4) combinations of materials from one or more of these groups. Often, no additional binder component need be employed.

Catalysts of the invention comprise molybdenum as a hydrogenation catalyst component. If desired, the catalyst may contain, as a minor portion of the hydrogenation catalyst component, a platinum-group metal, including one or more of platinum, palladium, rhodium, ruthenium osmium, and iridium. In any event, the molybdenum comprises at least about 60 atomic-percent, preferably at least about 80 atomic-percent to essentially all, of the hydrogenation metal (elemental basis) of the hydrogenation component. Often, any platinum group metal present is in an amount of 20 to 500 parts per million by mass (ppm-mass). Molybdenum (calculated on an elemental basis) generally comprises from about 0.1 to about 5 mass-% of the final catalyst. The hydrogenation metal may exist within the final catalyst composite as a compound such as an oxide, sulfide, halide, oxysulfide, etc., or as an elemental metal or in combination with one or more other ingredients of the catalyst composite.

It is within the scope of the present invention that the catalyst composites may contain other metal components. Such metal modifiers may include rhenium, tin, germanium, lead, cobalt, nickel, indium, gallium, zinc, uranium, dysprosium, thallium, and mixtures thereof. Catalytically effective amounts of such metal modifiers may be incorporated into the catalysts by any means known in the art to effect a homogeneous or stratified distribution. The catalysts of the present invention may contain a halogen component, comprising fluorine, chlorine, bromine or iodine or mixtures thereof, with chlorine being preferred. Preferably, however, the catalyst contains no added halogen other than that associated with other catalyst components.

The hydrogenation metal component may be incorporated into the catalyst composite in any suitable manner. One method of preparing the catalyst involves the utilization of a water-soluble, decomposable compound of the hydrogenation metal to impregnate the calcined sieve/binder composite. Alternatively, a hydrogenation metal compound may be added at the time of compositing the sieve component and binder. One useful process for making the catalysts comprises forming the catalyst composite without the molybdenum component and then impregnating or otherwise depositing on the composite with a molybdenum compound such as ammonium heptamolybdate, molybdenum trioxide, ammonium dimolybdate, molybdenum oxychloride, molybdenum halides, e.g., molybdenum chloride and molybdenum bromide, molybdenum carbonyl, phosphomolybdates, and heteromolybdic acids. Usually water soluble molybdenum compounds are selected as the source of the molybdenum component for the catalyst.

The catalyst composites are dried at a temperature of from about 100° to about 320° C. for a period of from about 2 to about 24 or more hours. If desired, the catalyst may be calcined at a temperature of from about 400° to about 650° C. in an air atmosphere for a period of from about 0.1 to about 10 hours. Steam may also be present during the calcination, e.g., from about 0.5 to 20, say, about 1 to 10, mol-% steam based on the air. Where the catalyst contains a minor amount, based on total hydrogenation metal, of platinum group metal, the resultant calcined composites often are subjected to a substantially water-free reduction step to ensure a uniform and finely divided dispersion of the optional metallic components. The reducing agent contacts the catalyst at conditions, including a temperature of from about 200° to about 650° C. and for a period of from about 0.5 to about 10 hours, effective to reduce substantially all of the platinum group metal component to the metallic state.

The catalysts are subjected to sulfiding to enhance activity. Sulfiding conditions are those in which the sulfiding agent is incorporated into the catalyst without forming sulfur dioxide. The sulfiding may be done during the catalyst preparation or thereafter, including as a pretreatment at catalyst start-up or during use of the catalyst. The sulfiding may be conducted in any convenient manner. For instance, a solid or sorbed sulfur-containing component, i.e., sulfiding agent, may be incorporated into the catalyst composite which decomposes during the catalyst preparation or during start-up or use of the catalyst. Alternatively, the formed catalyst may be contacted with a liquid or gaseous sulfiding agent under sulfiding conditions. Examples of sulfiding agents include hydrogen sulfide, carbonyl sulfide, carbon disulfide, salts, especially ammonium and organo salts, of sulfates, bisulfates, sulfites, and bisulfites, sulfur dioxide, sulfur trioxide, organosulfides, e.g., dimethyl sulfide, diethyl sulfide, and methyl ethyl sulfide; mercaptans, e.g., methyl mercaptan, ethyl mercaptan, and t-butyl mercaptan; thiophenes, e.g., tetrahydrothiophene.

The sulfiding conditions can vary widely and will depend upon the nature to the sulfiding agent and the extent of sulfiding desired. For instance, with oxygen-containing sulfur compounds, the sulfiding conditions should be sufficient to reduce the sulfur moiety to sulfide. The selection of the sulfiding conditions will also be influenced limits of feasibility at the location of the catalyst undergoing sulfiding. Thus, different conditions may be preferred where the sulfiding is being conducted after the catalyst has been installed in a reactor for the isomerization as would be preferred where the catalyst is at a facility for the manufacture of catalyst. In general, the sulfiding may be conducted over a temperature range of 0° to 800° C., preferably about 10° to 500° C. and a pressure of from about 10 to 5000 or more kPa absolute. The duration of the sulfiding will depend upon the other conditions of the sulfiding, e.g., the sulfiding agent, the concentration of the sulfiding agent, and sulfiding temperature, as well as the amount of sulfur to be incorporated into the catalyst. Usually the sulfiding is conducted for a period of time of at least about 10 minutes, and may, in the case of in situ sulfiding in an isomerization reactor, be continuous. Where the sulfiding is accomplished during the preparation of the catalyst, the sulfiding is usually done over a period of at least about 10 minutes, e.g., 10 minutes to 24 hours. Often, the sulfiding is done in the presence of hydrogen, e.g., at a partial pressure of about 10 to 5 MPa.

Where sulfiding is done while the catalyst is in an isomerization reactor, the sulfiding may be accomplished as a pretreatment or during the isomerization process itself. In the latter case, the sulfiding agent is usually provided in a low concentration, e.g., less than about 50, say about 0.001 to 20, ppm-mass of the feedstock.

Catalysts may be regenerated. Where the loss of catalytic activity is due to coking of the catalyst, conventional regeneration processes such as high temperature oxidation of the carbonaceous material on the catalyst may be employed. In an aspect of this invention, the catalyst suffering from the loss of isomerization activity may be regenerated by sulfiding to regain at least a portion of the isomerization activity. The regeneration may also reduce the naphthene make of the catalyst. Advantageously, the regeneration can occur while the catalyst is in the isomerization reactor, either by intermittently supplying sulfiding agent during the isomerization process at times that regeneration is sought, or by terminating the isomerization process and conducting a dedicated sulfiding. When in situ regeneration is desired, the sulfiding agent is usually provided in an amount between about 0.1 and 20 ppm-mass based upon the feed stream, for a time sufficient to introduce between about 0.5 and 3 atoms of sulfur per atom of molybdenum.

The Process

The feedstocks to the aromatics isomerization process of this invention comprise non-equilibrium xylene and ethylbenzene. These aromatic compounds are in a non-equilibrium mixture, i.e., at least one $C_8$ aromatic isomer is present in a concentration that differs substantially from the equilibrium concentration at isomerization conditions. Thus, a non-equilibrium xylene composition exists where one or two of the xylene isomers are in less than equilibrium proportion with respect to the other xylene isomer or isomers. The xylene in less than equilibrium proportion may be any of the para-, meta- and ortho-isomers. As the demand for para- and ortho-xylenes is greater than that for meta-xylene, usually, the feedstocks will contain meta-xylene. Generally the mixture will have an ethylbenzene content of about 1 to about 60 mass-%, an ortho-xylene content of 0 to about 35 mass-%, a meta-xylene content of about 20 to about 95 mass-% a para-xylene content of 0 to about 30 mass-%. Usually the non-equilibrium mixture is prepared by removal of para-, ortho- and/or meta-xylene from a fresh $C_8$ aromatic mixture obtained from an aromatics-production process. The feedstocks may contain other components, including, but not limited to naphthenes and acyclic paraffins, as well as higher and lower molecular weight aromatics.

The alkylaromatic hydrocarbons may be used in the present invention as found in appropriate fractions from various refinery petroleum streams, e.g., as individual components or as certain boiling-range fractions obtained by the selective fractionation and distillation of catalytically cracked or reformed hydrocarbons. Concentration of the isomerizable aromatic hydrocarbons is optional; the process of the present invention allows the isomerization of alkylaromatic-containing streams such as catalytic reformate with or without subsequent aromatics extraction to produce specified xylene isomers and particularly to produce para-xylene.

According to the process of the present invention, the feedstock, in the presence of hydrogen, is contacted with the catalyst described above. Contacting may be effected using the catalyst system in a fixed-bed system, a moving-bed system, a fluidized-bed system, and an ebullated-bed system or in a batch-type operation. In view of the danger of attrition loss of valuable catalysts and of the simpler operation, it is preferred to use a fixed-bed system. In this system, the feed mixture is preheated by suitable heating means to the desired reaction temperature, such as by heat exchange with another stream if necessary, and then passed into an isomerization zone containing catalyst. The isomerization zone may be one or more separate reactors with suitable means therebetween to ensure that the desired isomerization temperature is maintained at the entrance to each zone. The reactants may be contacted with the catalyst bed in upward-, downward-, or radial-flow fashion.

The isomerization is conducted under isomerization conditions including isomerization temperatures generally within the range of about 100° to about 550° C. or more, and preferably in the range from about 150° to 500° C. The pressure generally is from about 10 kPa to about 5 MPa absolute, preferably from about 100 kPa to about 3 MPa absolute. The isomerization conditions comprise the presence of hydrogen in a hydrogen to hydrocarbon mole ratio of between about 0.5:1 to 6:1, preferably about 1:1 or 2:1 to 5:1. One of the advantages of the processes of this invention is that relatively low partial pressures of hydrogen are still able to provide the sought selectivity and activity of the isomerization and ethylbenzene conversion. A sufficient mass of catalyst comprising the catalyst (calculated based upon the content of molecular sieve in the catalyst composite) is contained in the isomerization zone to provide a weight hourly space velocity with respect to the liquid feed stream (those components that are normally liquid at STP) of from about 0.1 to 50 $hr^{-1}$, and preferably 0.5 to 25 $hr^{-1}$.

The isomerization conditions may be such that the isomerization is conducted in the liquid, vapor or at least partially vaporous phase. For convenience in hydrogen distribution, the isomerization is preferably conducted in at least partially in the vapor phase. When conducted at least partially in the vaporous phase, the partial pressure of $C_8$ aromatics in the reaction zone is preferably such that at least about 50 mass-% of the $C_8$ aromatics would be expected to be in the vapor phase. Often the isomerization is conducted with essentially all the $C_8$ aromatics being in the vapor phase.

Usually the isomerization conditions are sufficient that at least about 50, preferably between about 60 and 80 or 90, percent of the ethylbenzene in the feed stream is converted. Generally the isomerization conditions do not result in a xylene equilibrium being reached. Where the isomerization process is to generate para-xylene, e.g., from meta-xylene, the feed stream contains less than 5 mass-% para-xylene and the isomerization product comprises a para-xylene to xylenes mole ratio of between about 0.233:1 to 0.25:1 preferably at least about 0.235:1.

The particular scheme employed to recover an isomerized product from the effluent of the reactors of the isomerization zone is not deemed to be critical to the instant invention, and any effective recovery scheme known in the art may be used. Typically, the isomerization product is fractionated to remove light by-products such as alkanes, naphthenes, benzene and toluene, and heavy byproducts to obtain a $C_8$ isomer product. Heavy byproducts include dimethylethylbenzene and trimethylbenzene. In some instances, certain product species such as ortho-xylene or dimethylethylbenzene may be recovered from the isomerized product by selective fractionation. The product from isomerization of $C_8$ aromatics usually is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described in U.S. Pat. No. 3,626,020, U.S. Pat. No. 3,696,107, U.S. Pat. No. 4,039,599, U.S. Pat. No. 4,184,943, U.S. Pat. No. 4,381,419 and U.S. Pat. No. 4,402,832, incorporated herein by reference.

EXAMPLES

The following examples are presented only to illustrate certain specific embodiments of the invention, and should not be construed to limit the scope of the invention as set forth in the claims. There are many possible other variations, as those of ordinary skill in the art will recognize, within the spirit of the invention.

EXAMPLE I

Catalyst samples are prepared.

Catalyst A: Steamed and calcined aluminum-phosphate-bound MFI zeolite spheres are prepared using the method of Example I in U.S. Pat. No. 6,143,941. The pellets are impregnated with an aqueous solution of ammonium heptamolybdate, dried and calcined in dry air for 2 hours at 538° C. to give 1.0 mass-% Mo on the catalyst.

Catalyst B: Steamed and calcined aluminum-phosphate-bound MFI zeolite spheres are prepared using the method of Example I in U.S. Pat. No. 6,143,941. The pellets are impregnated with 1 mass-% Mo from an aqueous solution of ammonium heptamolybdate, dried and calcined in dry air for 2 hours at 538° C. The catalyst is contacted with 10 mass-% $H_2S$ in $H_2$ for 6 hours at 415° C. to give a sulfur level of 0.7 mass-% on the catalyst.

Catalyst C: Steamed and calcined aluminum-phosphate-bound MFI zeolite spheres are prepared using the method of Example I in U.S. Pat. No. 6,143,941. The pellets are impregnated with 1 mass-% Mo from an aqueous solution of ammonium heptamolybdate, dried and calcined in dry air for 2 hours at 538° C. The catalyst is contacted with $H_2S$ at ambient temperature to give a sulfur level of 0.7 mass-% on the catalyst.

Catalyst D: Steamed and calcined aluminum-phosphate-bound MFI zeolite spheres are prepared using the method of Example I in U.S. Pat. No. 6,143,941. The pellets are impregnated with an aqueous solution of tetra-ammine platinum chloride to give 0.038 mass-% platinum after drying and calcination at 538° C.

EXAMPLE II

Catalysts A, B, C and D are evaluated in a pilot plant for the isomerization of a feed stream containing 7 mass-% ethylbenzene, 1 mass-% para-xylene, 22 mass-% ortho-xylene and 70 mol-% meta-xylene. The pilot plant runs are at a hydrogen to hydrocarbon ratio of 4:1, total pressure of 1200 kPa, and weight hourly space velocity of 10 based on the total amount of catalyst loaded. The pilot plant runs are summarized in Table 1. The product data are taken at approximately 50 hours of operation.

TABLE 1

| | Catalyst | | | |
|---|---|---|---|---|
| | A (comparative) | B | C | D (comparative) |
| EB Conversion, % | 75 | 75 | 75 | 75 |
| WABT, ° C. | 399 | 388 | 390 | 404 |
| Para-xylene/xylene | 23.3 | 23.7 | 23.6 | 23.7 |
| Xylene loss, % | 2.7 | 2.1 | 2.5 | 3.1 |
| Toluene + Trimethylbenzene, mass-% yield | 1.8 | 1.9 | 2.5 | 2.1 |
| $C_6$ Naphthenes, mass-% yield | 0.015 | 0.005 | 0.002 | 0.080 |

EXAMPLE III

During a pilot plant evaluation using feed and process conditions given in Example II, Catalyst A is held at 404° C. and is contacted with feed which contains 1 mass-ppm sulfur added as thiophene for sufficient time to pass 2 moles sulfur per mole molybdenum. After this time, the catalyst performance is re-evaluated with feed without added sulfur. The results are shown in Table 2.

TABLE 2

| | Prior to sulfiding | After in-situ sulfiding: |
|---|---|---|
| EB Conversion, % | 75 | 75 |
| WABT, ° C. | 399 | 399 |
| Para-xylene/xylene | 23.3 | 23.5 |
| Xylene loss, % | 2.7 | 2.0 |
| Toluene + Trimethylbenzene, mass-% yield | 1.8 | 1.8 |
| $C_6$ Naphthenes, mass-% yield | 0.015 | 0.002 |

What is claimed is:

1. A process for dealkylating ethylbenzene and isomerizing xylene in a feed stream comprising ethylbenzene and a non-equilibrium mixture of one or more xylenes comprising contacting the feed stream with the catalyst comprising an amount of molecular sieve having a pore diameter of from about 4 to 8 angstroms and an amount of molybdenum hydrogenation component which has been subjected to sufficient sulfiding to enhance the xylene isomerization activity wherein the catalyst comprises sulfur in a S:Mo atomic ratio of up to about 3:1 under dealkylation and isomerization conditions including the presence of hydrogen to provide a product.

2. The process of claim 1 wherein the feed stream comprises between about 1 and 60 mol-% ethylbenzene.

3. The process of claim 1 wherein the feed stream comprises meta-xylene.

4. The process of claim 1 wherein the molecular sieve in the catalyst comprises pentasil zeolite.

5. The process of claim 4 wherein the hydrogen to hydrocarbon ratio is about 0.5:1 to 6:1.

6. The process of claim 5 wherein at least about 60 mass-% of the ethylbenzene is converted.

7. The process of claim 6 wherein the feed stream contains less than 5 mass-% para-xylene and the isomerization product comprises a para-xylene to xylenes mole ratio of at least about 0.233:1.

8. The process of claim 1 wherein the catalyst comprises sulfur in a S:Mo atomic ratio of up to about 0.1:1 to 2:1.

9. The process of claim 1 wherein the feed comprises sulfiding agent.

10. The process of claim 2 wherein the sulfiding agent is provided intermittently.

* * * * *